(12) United States Patent
Gupta et al.

(10) Patent No.: US 11,688,521 B2
(45) Date of Patent: Jun. 27, 2023

(54) RISK STRATIFICATION FOR ADVERSE HEALTH OUTCOMES

(71) Applicant: Health Solutions Research, Inc., Rockville, MD (US)

(72) Inventors: Ajay Kumar Gupta, Potomac, MD (US); Ramani Peruvemba, McLean, VA (US)

(73) Assignee: HEALTH SOLUTIONS RESEARCH, INC., Rockville, MD (US)

( * ) Notice: Subject to any disclaimer, the term of this patent is extended or adjusted under 35 U.S.C. 154(b) by 1007 days.

(21) Appl. No.: 16/429,550

(22) Filed: Jun. 3, 2019

(65) Prior Publication Data

US 2020/0005946 A1     Jan. 2, 2020

Related U.S. Application Data (63) Continuation-in-part of application No. 16/126,537, filed on Sep. 10, 2018, and a continuation-in-part of application No. 16/024,387, filed on Jun. 29, 2018, now Pat. No. 11,177,040.

(51) Int. Cl.
| | |
|---|---|
| *G16H 50/70* | (2018.01) |
| *G16H 50/30* | (2018.01) |
| *G06F 17/18* | (2006.01) |
| *G06F 16/9035* | (2019.01) |
| *G16H 10/60* | (2018.01) |

(52) U.S. Cl.
CPC ......... *G16H 50/70* (2018.01); *G06F 16/9035* (2019.01); *G06F 17/18* (2013.01); *G16H 10/60* (2018.01); *G16H 50/30* (2018.01)

(58) Field of Classification Search
CPC ........ G16H 50/70; G16H 10/60; G16H 50/30; G06F 16/9035; G06F 17/18
See application file for complete search history.

(56) References Cited

U.S. PATENT DOCUMENTS

| | | | |
|---|---|---|---|
| 8,758,238 | B2 | 6/2014 | Clapp |
| 9,152,918 | B1 | 10/2015 | McNair |
| 2002/0183965 | A1* | 12/2002 | Gogolak |
| 2005/0203773 | A1* | 5/2005 | Soto et al. |
| 2005/0131740 | A1 | 6/2005 | Massenzio et al. |
| 2006/0129427 | A1 | 6/2006 | Wennberg |

(Continued)

FOREIGN PATENT DOCUMENTS

| | | |
|---|---|---|
| WO | 2016/172614 | 10/2016 |

OTHER PUBLICATIONS

Chen et al., "Reality mining: A prediction algorithm for disease dynamics based on mobile big data," Information Sciences 379 ( 2017) 82-93 (Year: 2017) ; Cited in Notice of Allowance issued in U.S. Appl. No. 16/024,387.

(Continued)

*Primary Examiner* — Michael Tomaszewski
*Assistant Examiner* — William T. Monticello
(74) *Attorney, Agent, or Firm* — Hamre, Schumann, Mueller & Larson, P.C.

(57) ABSTRACT

Methods and systems to stratify risks for adverse health outcomes include aggregating data sets culled over a predetermined period of time; adjusting at least two variables within the aggregated data sets; and executing a regression analysis to identify an average causal effect between aggregated variables against at least one particular adverse health outcome.

14 Claims, 6 Drawing Sheets

(56) References Cited

U.S. PATENT DOCUMENTS

| | | | |
|---|---|---|---|
| 2008/0091471 A1 | 4/2008 | Michon et al. | |
| 2008/0228824 A1* | 9/2008 | Kennedy et al. | |
| 2009/0216564 A1* | 8/2009 | Rosenfeld | |
| 2011/0288886 A1 | 11/2011 | Whiddon et al. | |
| 2013/0185097 A1* | 7/2013 | Saria et al. | |
| 2013/0339053 A1* | 7/2013 | Jacobs et al. | |
| 2013/0197942 A1 | 8/2013 | Chiu | |
| 2014/0081652 A1* | 4/2014 | Klindworth et al. | |
| 2014/0236668 A1 | 8/2014 | Young et al. | |
| 2015/0064137 A1 | 3/2015 | Lichtsteiner et al. | |
| 2015/0213225 A1 | 7/2015 | Amarasingham et al. | |
| 2015/0242586 A1 | 8/2015 | Kagen | |
| 2016/0110512 A1 | 4/2016 | Adjaoute | |
| 2016/0314256 A1 | 10/2016 | Su et al. | |
| 2016/0378932 A1 | 12/2016 | Sperling et al. | |
| 2017/0004275 A1 | 1/2017 | Mehta et al. | |
| 2017/0061077 A1 | 3/2017 | Cline et al. | |
| 2017/0076058 A1 | 3/2017 | Stong | |
| 2017/0103172 A1* | 4/2017 | Fink et al. | |
| 2017/0109493 A1 | 4/2017 | Hogg et al. | |
| 2017/0132371 A1 | 5/2017 | Amarasingham et al. | |
| 2017/0286622 A1 | 10/2017 | Cox et al. | |
| 2017/0351834 A1 | 12/2017 | Cahan et al. | |
| 2018/0137235 A1 | 5/2018 | Meshkin | |
| 2018/0330824 A1* | 5/2018 | Athey et al. | |
| 2019/0088356 A1 | 3/2019 | Oliver et al. | |
| 2019/0133536 A1* | 5/2019 | Roberts et al. | |
| 2019/0182749 A1 | 6/2019 | Breaux et al. | |
| 2020/0225189 A1 | 7/2020 | Verma et al. | |
| 2020/0349324 A1 | 11/2020 | Ostby et al. | |
| 2021/0166819 A1 | 6/2021 | Gupta et al. | |
| 2021/0319884 A1 | 10/2021 | Day et al. | |
| 2021/0366621 A1 | 11/2021 | Miff et al. | |
| 2022/0059242 A1 | 2/2022 | Schneider et al. | |

OTHER PUBLICATIONS

Chang et al., "Mobility network models of COVID-19 explain inequities and inform reopening", Nature, vol. 589, 44 pages, Nov. 10, 2020, available at https://www.nature.com/articles/s41586-020-2923-3.

* cited by examiner

RISK STRATIFICATION FOR ADVERSE HEALTH OUTCOMES

CROSS-REFERENCE TO RELATED APPLICATIONS

This application is a continuation-in-part of U.S. patent application Ser. No. 16/126,537, filed on Sep. 10, 2018; which is a continuation-in-part of U.S. patent application Ser. No. 16/024,387, filed on Jun. 29, 2018, the entire disclosures of both are hereby incorporated by reference herein.

TECHNICAL FIELD

The present disclosure relates to a data analytic approach to establishing risk stratification for adverse health outcomes.

BACKGROUND

It is estimated that, annually in the United States, at least 700 women die of complications related to pregnancy and childbirth, and more than 50,000 women experience a life-threatening complication (severe maternal morbidity). It is further estimated that maternal mortality in the United States almost doubled between 1990 and 2014 at a time when 157 of 183 countries in a World Health Organization (WHO) study reported decreases in maternal mortality. In medical circles, both maternal and infant mortality are regarded as being indicative of a nation's health and quality of health care. While the United States saw an overall improvement in its infant mortality rate between 2005 and 2014, declining 15% from the recent high of 6.86 infant deaths per 1,000 live births to 5.82 in 2014, trends in infant and maternal mortality rates did not decline as significantly when compared to other countries of similar socioeconomic development.

SUMMARY

In accordance with at least one embodiment, a method to stratify risks for adverse health outcomes includes aggregating data sets culled over a predetermined period of time; adjusting at least two variables within the aggregated data sets; and executing a regression analysis to identify an average causal effect between aggregated variables against at least one particular adverse health outcome.

In accordance with at least one other embodiment, a non-transitory computer-readable medium has computer-readable instructions stored thereon that, if executed by a computing device, cause the computing device to aggregate health data regarding a general population in a particular municipality over a predetermined period of time; adjust at least two variables within the aggregated health data to eliminate subjects outside of an area of interest; and execute a regression analysis to identify an average causal effect between aggregated variables against at least one particular adverse health outcome for subjects not eliminated from the aggregated health data.

BRIEF DESCRIPTION OF THE DRAWINGS

In the detailed description that follows, embodiments are described as illustrations only since various changes and modifications will become apparent to those skilled in the art from the following detailed description. The use of the same reference numbers in different figures indicates similar or identical items.

DETAILED DESCRIPTION

In the following detailed description, reference is made to the accompanying drawings, which form a part of the description. In the drawings, similar symbols typically identify similar components, unless context dictates otherwise. Furthermore, unless otherwise noted, the description of each successive drawing may reference features from one or more of the previous drawings to provide clearer context and a more substantive explanation of the current example embodiment. Still, the example embodiments described in the detailed description, drawings, and claims are not intended to be limiting. Other embodiments may be utilized, and other changes may be made, without departing from the spirit or scope of the subject matter presented herein. It will be readily understood that the aspects of the present disclosure, as generally described herein and illustrated in the drawings, may be arranged, substituted, combined, separated, and designed in a wide variety of different configurations, all of which are explicitly contemplated herein.

In some embodiments presented herein, identification of social determinants of adverse health outcomes may be utilized to stratify particular demographics of people that may be afflicted with particular adverse health outcomes, demographics of a community, environment, e.g., for those people, etc. As described and recited herein, a stratification, i.e., multivariable algorithm utilizing weighted factors, may be established to identify expectant mothers who may be prone to risk of complications that are related to pregnancy or child-delivery and lead to adverse health outcomes such as maternal mortality, maternal morbidity, infant mortality, and low birth weight for a child. As a result, one of multiple benefits may include the identification of high-risk expectant mothers whose pregnancies may be monitored and/or managed to reduce or even eliminate risks that lead to such adverse health outcomes for mother and/or child.

As referenced herein, maternal mortality may refer to death during pregnancy or within 42 days of termination of the pregnancy, irrespective of the duration and site of the pregnancy, from any cause related to or aggravated by the pregnancy or its management but not from accidental or incidental causes.

As referenced herein, maternal morbidity may refer to unexpected outcomes of labor and delivery that result in significant short- or long-term consequences to a woman's health.

As referenced herein, infant mortality may refer to the death of an infant before his or her first birthday. Infant mortality is often considered to be an indicator of a country's health status.

As referenced herein, low birth weight may refer to babies who are born weighing less than 5 pounds and 8 ounces (2,500 grams). The average newborn weighs about 8 pounds. Future complications may include issues within internal organ function, dangerously low blood sugar, hypothermia, and trouble eating.

According to the methods, programs, and systems described and recited herein, data from municipalities, from the national and state levels down to counties, cities, and towns, ZIP code, census tracks, and census blocks may be collected and culled to identify a list of drivers and risk factors for maternal and infant mortality. When analyzing disparities across demographic and social indicators of health, there exist a variety of factors that contribute to maternal and infant mortality rates. The relationship between maternal and infant health occurs linearly; that is, health outcomes for a baby correlate to those of the mother. More particularly, mortality among infants may be driven, in part, by the health status of the mother. With a stated public health goal of improving infant mortality rates, a focus must include improving morbidity and mortality rates for mothers of infants.

Mortality among infants may be further influenced by biological, genetic, and environmental factors. Such causes may be determined by a mother's behavior during the early developmental stages of pregnancy. However, some factors may not be immediately obvious when examining maternal health. Improvements in maternal health may not adequately influence others.

An examination of state data by risk factors, including race and ethnicity as well as detailed causes of death may help better identify state-level disparities. Described and recited herein are methods, programs, and systems to isolate leading risk factors for maternal and infant mortality considering disparities across race, socio-economic status, health care access, health status, and other factors to develop a comprehensive risk stratification that can identify an expecting mother's overall level of risk for herself and her child. This will help the healthcare community improve care for those at greatest risk and help lower our national maternal and infant mortality rate.

Figure 1:
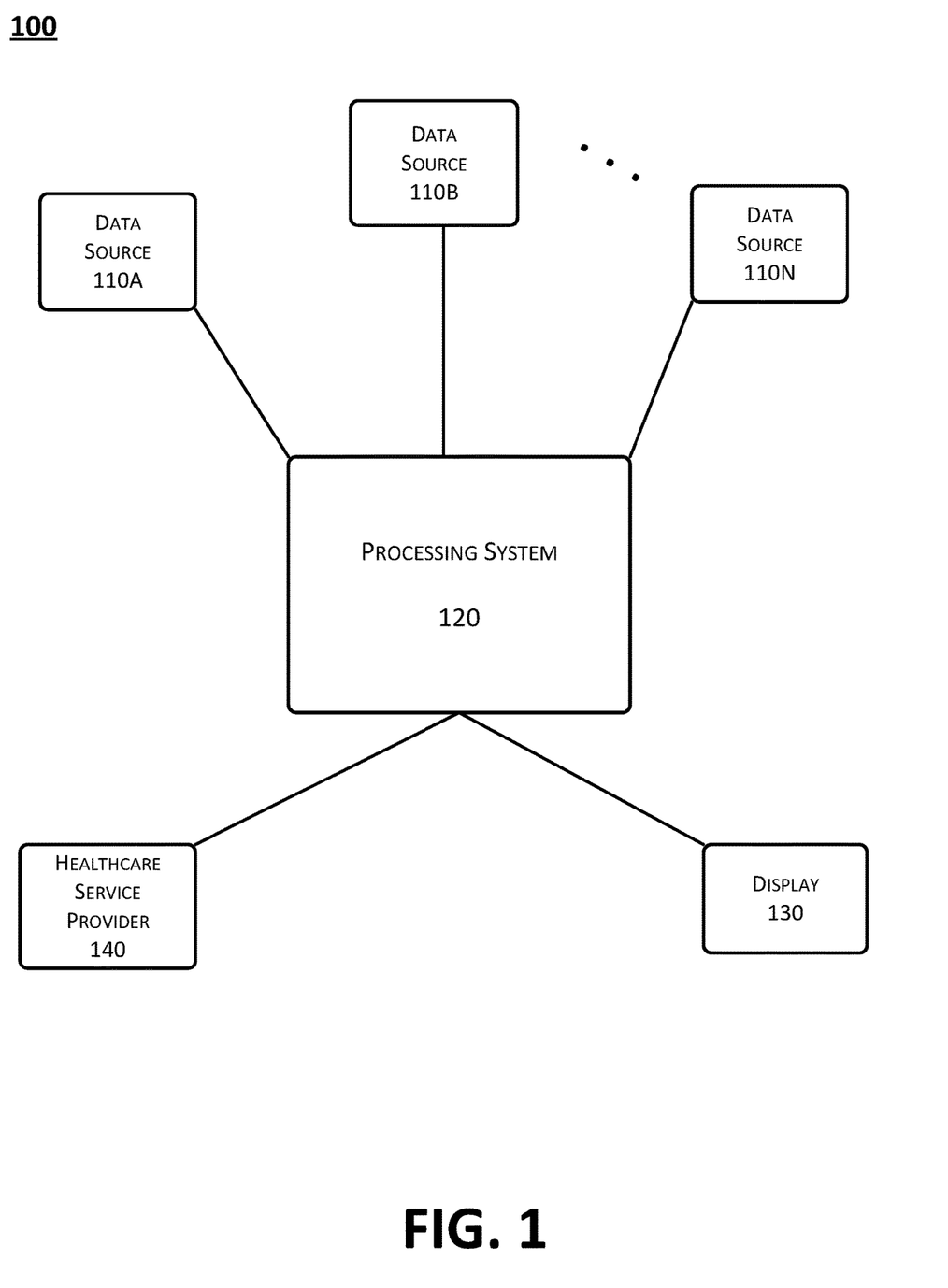
FIG. 1 shows an example configuration of a system by which a risk stratification for adverse health outcomes may be implemented, arranged in accordance with at least some embodiments described herein.

FIG. 1 shows an example configuration of a system 100 by which risk stratification for adverse health outcomes may be implemented, arranged in accordance with at least some embodiments described herein. FIG. 1A shows a plurality of data sources 110a, 110b . . . 110n (collectively, "data sources 110" hereafter), which may be communicatively coupled to a processing system 120. Processing system 120 may be communicatively coupled to at least one of a display 130 and a health care servicer 140 (e.g., a hospital or other point-of-care provider). By way of example and without limitation, one or more of the communicative couplings may be wired or wireless connections as would be understood by one of ordinary skill in the art.

The present description and recitation may have relevance for myriad possible adverse health outcomes. However, for the sake of providing a cogent explanation, the example adverse health outcomes specifically referenced herein include maternal morbidity, maternal mortality, infant morbidity, and infant mortality. However, these examples are not exclusive to the methodologies, programs, applications, apparatuses, and systems described and recited herein.

Data sources 110A, 110B . . . 110N may refer to, but not be limited to, e.g., state health departments and national level health repositories, America's Health Rankings, County Health Rankings, CDC Wonder, World Health Organization (WHO), The United Nations, Kaiser Family Foundation, other non-profits, etc. Further, not only are the systems described, recited, and foreseen herein not limited to the data sources listed above, but they are not limited in quantity to those shown in FIG. 1. Further still, unless context otherwise requires, the description and recitation henceforth may refer to the singular "data source 110" without being limiting.

The data received from one or more instances of data source 110 may include, but not be limited to vital health statistics and social determinants of health resources that are available on municipality-levels, e.g., national level, state level, counties, cities, towns, ZIP codes, census tracks, and census blocks. As discussed below, the collection of statistical reports for maternal and infant health, behavior, and demographic data may be utilized to implement risk stratification.

To establish a risk stratification for adverse health outcomes such as maternal morbidity, maternal mortality, infant morbidity, and infant mortality, examples of information that data sources 110 may provide may include various socio-environmental and biological risk factors for those in position to provide assistance, such as, e.g., healthcare service provider 140. Those risk factors may include, but not be limited to: racial disparities that may contribute to access to quality health services; non-communicable diseases incurred before and/or during pregnancy that may lead to complications for the child; socio-economic variables such as social class, income, access to insurance, etc.; drug use before and/or during pregnancy; and venous thromboembolism, which is a medical complication that may occur during pregnancy, delivery, or puerperium that may lead to a mother's fatality.

These and other data may be obtained from other sources, and in the future additional sources of such data may become available and used as well.

Figure 2:
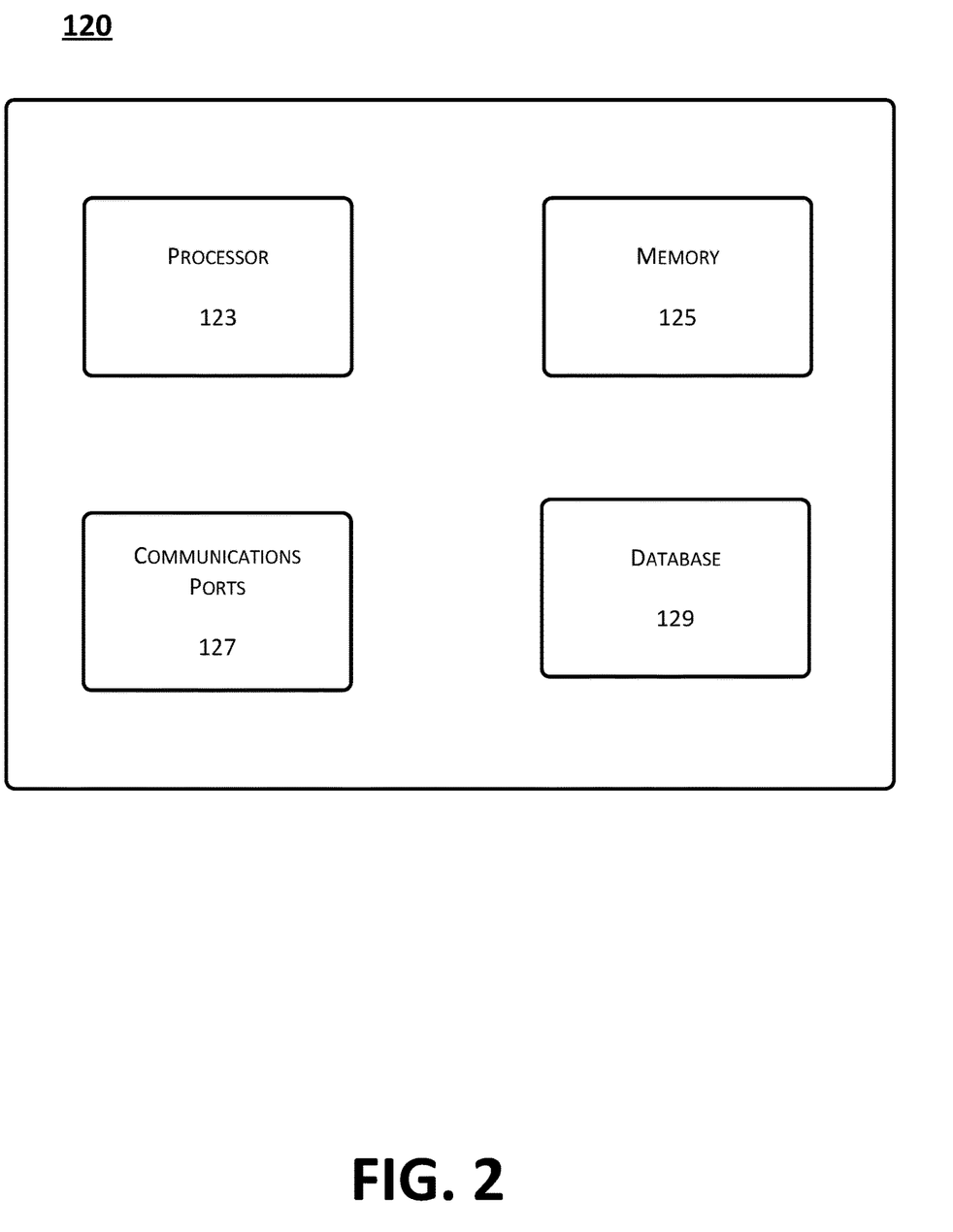
FIG. 2 shows an example configuration of a processing system that may be implemented, arranged in accordance with at least some embodiments described herein.

FIG. 2 shows an example configuration of processing system 120 that may be implemented, arranged in accordance with at least some embodiments described herein. In one or more embodiments, processing system 120 may include one or more processors or computing devices 123 (collectively, "processor" as used herein), a system memory 125, communication ports 127 to acquire data from one or more of data sources 110, and a database 129. Processing system 120 may be configured and arranged to implement an information system platform with a data analytic engine as discussed below. Data acquired from data sources 110 may be added to database 129. The stored data may be analyzed using data analytics and formatted for output for any suitable purpose, such as for further analysis or review (e.g., personal or machine) either locally or remotely (e.g., into the electronic health record (EHR) system or other clinical applications at a hospital or healthcare service provider 140).

In one or more embodiments, the model gathers data from a general population in a particular municipality; and culls the data to identify women at risk for an adverse health outcome, e.g., maternal morbidity, maternal mortality, infant morbidity, and infant mortality.

Processing flow 200 may include one or more operations, actions, or functions depicted by one or more blocks 205, 210, 215, and 220. Although illustrated as discrete blocks, various blocks may be divided into additional blocks, combined into fewer blocks, or eliminated, depending on the desired implementation. As a non-limiting example, the description of processing flow 200, corresponding to the depiction thereof in FIG. 2 and performed by processing system 120 in one or more embodiments described herein, pertains to identifying an average causal effect between aggregated variables against at least one particular adverse health outcome. As described and recited herein, such an adverse health outcome may include at least one of maternal morbidity, maternal mortality, infant morbidity, and infant mortality. Processing may begin at block 205.

Block 205 (Aggregate Data Sets) may refer to processing system 120 receiving data of a subject population (X) from data sources 110 via communication ports 127. Subject population (X) may include a population of a particular municipality, including a particular town, city, county, state, etc.

Pertinent health statistics and social determinants of health resources that are available on municipality-levels, e.g., national, state, and county, have been identified. This collection of statistical reports for maternal and infant health, behavior, and demographic data may be utilized to implement risk stratification. The aggregated data may be analyzed through a geospatial data analytic platform to accurately establish a stratification for identifying those at high risk of facing maternal complications and/or labor & delivery-related adverse health outcomes, which may apply to pregnancy, labor, delivery, and even the period of up to one-year post-birth. The datasets aggregated for analysis may be received from data sources 110, e.g., state health departments and national level health repositories, America's Health Rankings, County Health Rankings, CDC Wonder, and other sources including potential future data sources yet to be identified as well as new sources that will be created or established. These reports may include analyses, surveys, individual and regional level data that includes comprehensive sets of behaviors, public and health policies, community and environmental conditions, and clinical care data to provide a better understanding of the national status of maternal and infant health. Data elements may include but are not limited to, e.g., women of childbearing age, fertility, infant mortality, live births, maternal mortality, low birth weight, preterm birth, and maternal drug and alcohol use, etc. Processing may proceed from block 205 to block 210.

Block 210 (Adjust Variables Within Data Sets) may refer to processor 123 applying age-gender specific rates to a standard age-sex distribution to eliminate differences in crude rates in populations of interest that result from differences in the populations' demographic distributions. This adjustment is implemented to extract women of childbearing age data from raw data in the aggregated data sets. Further, the adjustment of variables described herein is not limiting, but rather is provided as an example of analytic processing contemplated within the scope and spirit of the embodiments disclosed herein.

Further, age-sex-adjustment weights may be applied, based on population distribution across various municipalities, e.g., states and counties. Age-gender mortality data may be taken from available data sources 110. To control for differing data gathering capacities, health indicator (HI) rates may be calculated using state vital statistics records and state population records.

The calculation may be implemented as follows:

$$\text{standardized } HI \text{ }rate_{c,t} = 100{,}000 * \sum \frac{(Deaths_{c,t,a,s})}{(Popuation_{c,t,a,s})} * w_{a,s},$$

$$\text{given } w_{a,s} = \frac{Populations^*_{a,s}}{Population^*_{Total}} \text{ and } \sum w_{a,s} = 1$$

where country-year-age-gender-specific (c,t,a,s) HI rate (HI/population) data are multiplied by age-gender-specific (a,s) standard weights (w). After weighting, age-gender pairs are summed up and multiplied by 100,000 to get one age-sex-adjusted death rate for each municipality-year, e.g., county. Processing may proceed from block 210 to block 215.

Block 215 (Execute Regression Analysis) may refer to processor 123 executing a regression analysis to determine geospatial contributors of morbidity and mortality to identify high-risk mothers and infants. Visually representing health and socio-demographic indicators through geospatial mapping may provide an innovative methodology for data interpretation. After the aggregation of appropriate health and demographic data, processor 123 may map relevant numerator and denominator data elements against each other. This level of visualization facilitates identification of key localities of at-risk mothers, as well as what might be the contributing factor to those adverse outcomes in question. It should be noted that a regression analysis is disclosed herein as a non-limiting example of the type of analysis that may be implemented for risk stratification. Alternative implementations for identifying mathematical and data analytic techniques to determine geospatial contributors of morbidity and mortality that identify high-risk mothers and infants are contemplated by the embodiments described herein. However, for the purpose of providing an enabling disclosure, reference may be made to the example of regression analysis, with the understanding that other forms of analysis may be utilized for the same purposes. Processing may proceed from block 215 to block 220.

Block 220 (Identification of Causal Effect(s)) may refer to processor 123 utilizing results of the regression analysis to generate a correlation table using particular health and demographic data. The analysis facilitates quantification of a degree of correlation between individual risk factors against one or more relevant adverse outcomes during pregnancy with a Pearson product-moment correlation coefficient. Though disclosed as a non-limiting example of the data processing that may be implemented for the solutions described and even contemplated herein, the Pearson correlation coefficient may take a range of values from +1 to −1; a value of 0 indicates that there is no association between the two variables; and a value greater than 0 indicates a positive association. That is, as the value of one variable increases, so does the value of the other variable. A value less than 0 indicates a negative association; that is, as the value of one variable increases, the value of the other variable decreases.

Thus, leveraging data provided by data sources 110 may produce a correlation analysis of risk factors impacting maternal and infant mortality in a given municipality.

Figure 6:
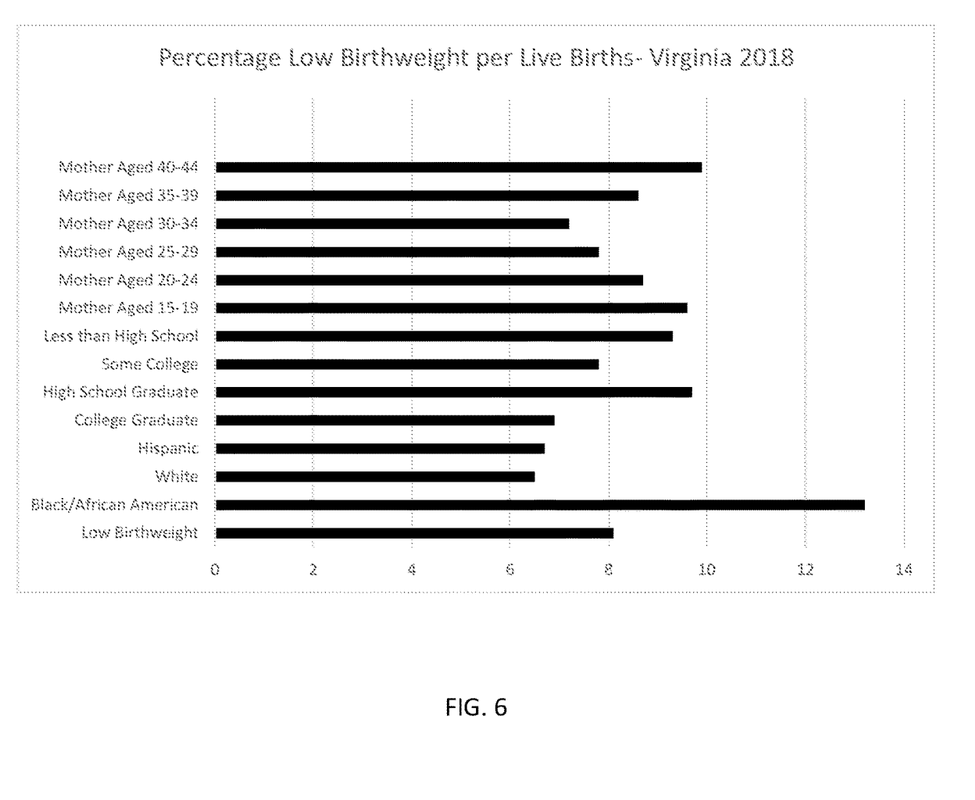
FIG. 6 shows the percentage of low birthweight per live births that may be used in an example embodiment.

As a non-limiting example, as shown in FIG. 6 and the following Table below, in the Commonwealth of Virginia, Hispanic women, Alaskan Natives, and African American women see a higher correlation to low birth weight and infant mortality compared to White and Asian Women. Initial analysis suggests that there is a negative correlation between being an Asian woman, and the states infant health indicators.

Additional initial analysis suggests that women of child-bearing age who have completed a bachelor's degree or a Professionals degree see a negative association to both low birth weight and infant mortality. In contrast, women of child-bearing age who are a high school graduate or who have not completed high school, see a slightly higher level of correlation to low birth weight and infant mortality. There is little to no substantive correlation to the completion of some college or an Associate's degree.

TABLE

Race and Education Indicators against Low Birthweight and Infant Mortality

|  | Hispanic | African American | White | Asian | Alaskan Natives |
|---|---|---|---|---|---|
| Race Indicators (Rate of Birth per 1000) | | | | | |
| Low Birthweight | 0.191683971 | 0.24720879 | 0.097838142 | −0.204082456 | 0.139465402 |
| Infant Mortality | 0.132576875 | 0.03057372 | 0.071687573 | −0.208143045 | 0.255196744 |
| Education Indicators (Rate of Birth per 1000) | | | | | |
|  | <High School | High School Graduate | Some College/ Associates | Bachelors Degree | Graduates/ Professional Degree |
| Low Birthweight | 0.169957233 | 0.265293111 | 0.065964356 | −0.229413536 | −0.180324622 |
| Infant Mortality | 0.176388783 | 0.090078234 | 0.035420113 | −0.19877824 | −0.231990362 |

By this example, the methodologies described herein reveal that, between 1987-2014, pregnancy-related mortality rates in the U.S. more than doubled from 7.2 to 18 per 100,000 live births. In view of 157 out of 183 countries showing a decline in maternal death rates, this marked increase within the U.S. is out of step with the international health community. By the example methodologies, programs, and systems described and recited herein, behaviors and conditions contributing to these high death rates may be identified and isolated, thus potentially driving health policies and reduce preventable deaths.

Figure 3:
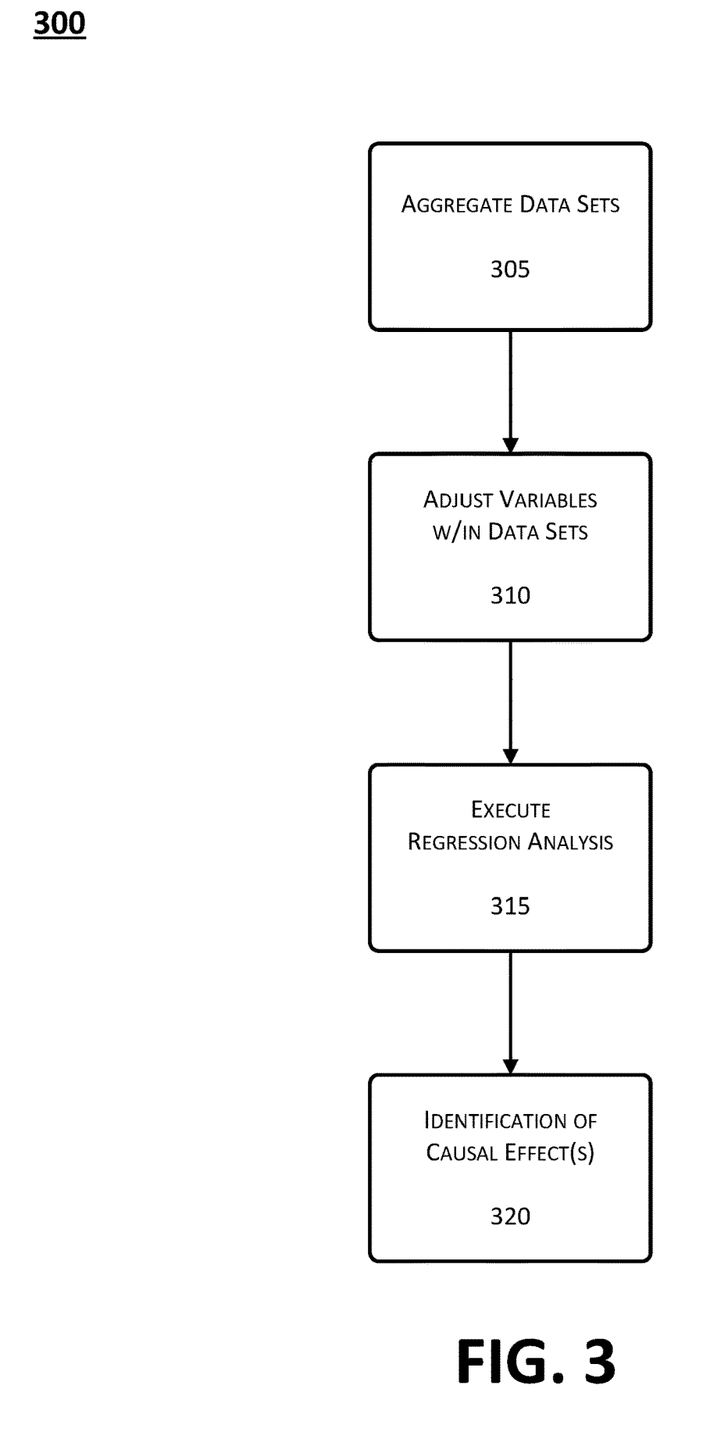
FIG. 3 shows an example processing flow by which a model to establish risk stratification for adverse health outcomes may be developed, arranged in accordance with at least some embodiments described herein.
Figure 4:
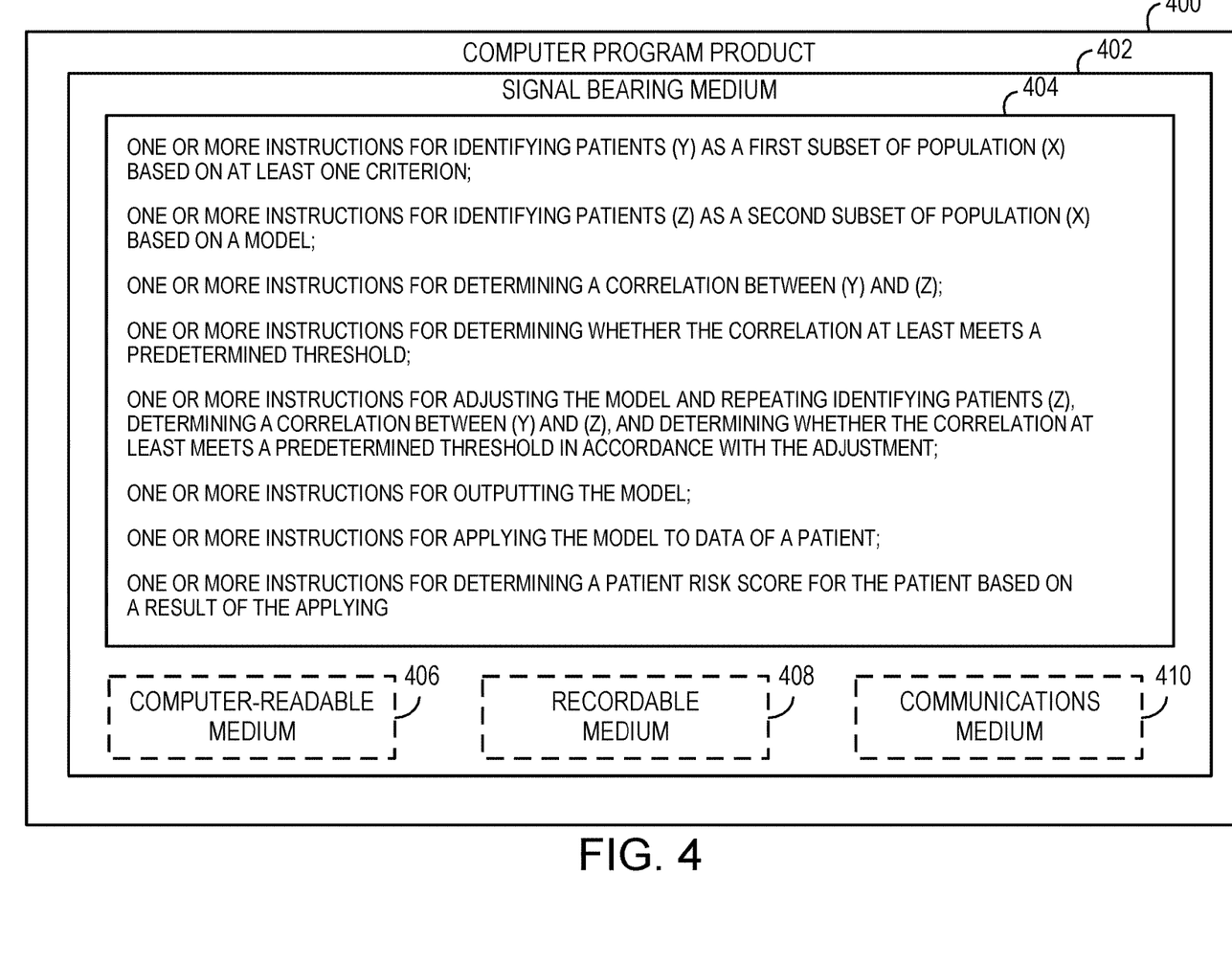
FIG. 4 shows an example computer program product that may be utilized to establish a risk stratification for adverse health outcomes, arranged in accordance with at least some embodiments described herein.

FIG. 4 illustrates computer program products that may be utilized to provide a scheme for stratifying risks for adverse health outcomes, arranged in accordance with at least some embodiments described herein. Program product 400 may include a signal bearing medium 402. Signal bearing medium 402 may include one or more instructions 404 that, when executed by, for example, a processor, may provide the functionality described above with respect to FIGS. 1-3. By way of example, but not limitation, instructions 404 may include: one or more instructions to aggregate data sets culled over a predetermined period of time; adjust at least two variables within the aggregated data sets; and execute a regression analysis to identify an average causal effect between aggregated variables against at least one particular adverse health outcome.

In some implementations, signal bearing medium 402 may encompass a computer-readable medium 406, such as, but not limited to, a hard disk drive, a CD, a DVD, a flash drive, memory, etc. In some implementations, signal bearing medium 402 may encompass a recordable medium 408, such as, but not limited to, memory, read/write (R/W) CDs, R/W DVDs, etc. In some implementations, signal bearing medium 402 may encompass a communications medium 410, such as, but not limited to, a digital and/or an analog communication medium (e.g., a fiber optic cable, a waveguide, a wired communications link, a wireless communication link, etc.). Thus, for example, computer program product 400 may be conveyed to one or more modules of processor 123 by an RE signal bearing medium, where the signal bearing medium is conveyed by a wireless communications medium (e.g., a wireless communications medium conforming with the IEEE 802.11 standard).

Figure 5:
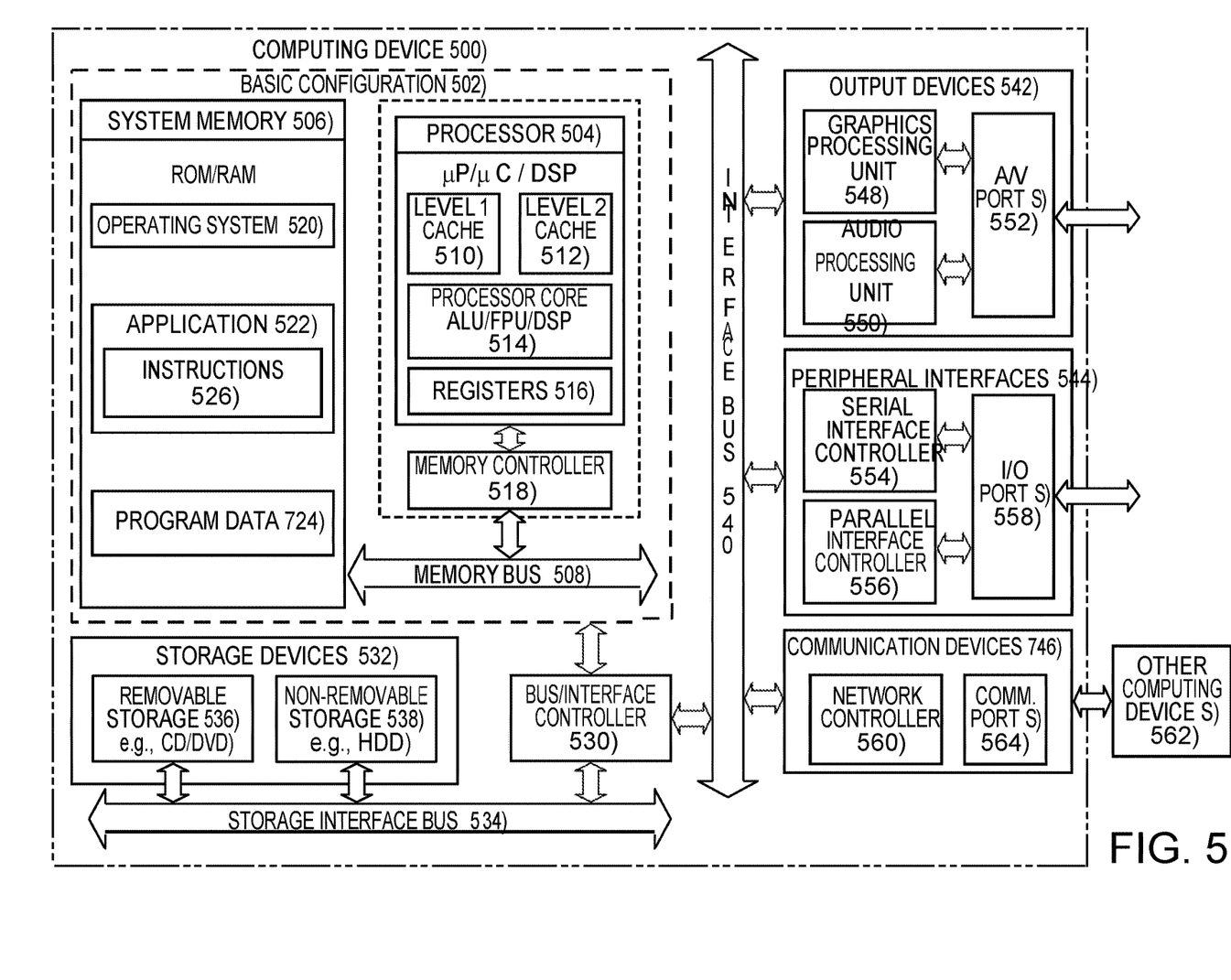
FIG. 5 shows a block diagram illustrating an example computing device by which various example solutions described herein may be implemented.

FIG. 5 shows a block diagram illustrating an example computing device 500 by which various example solutions described herein may be implemented, arranged in accordance with at least some embodiments described herein. In a very basic configuration 502, computing device 500 typically includes one or more processors 504 and a system memory 506. A memory bus 508 may be used for communicating between processor 504 and system memory 506.

Depending on the desired configuration, processor 504 may be of any type including but not limited to a microprocessor (µP), a microcontroller (µC), a digital signal processor (DSP), or any combination thereof. Processor 504 may include one or more levels of caching, such as a level one cache 510 and a level two cache 512, a processor core 514, and registers 516. An example processor core 514 may include an arithmetic logic unit (ALU), a floating-point unit (FPU), a digital signal processing core (DSP Core), or any combination thereof. An example memory controller 518 may also be used with processor 504, or in some implementations memory controller 518 may be an internal part of processor 504.

Depending on the desired configuration, system memory 506 may be of any type including but not limited to volatile memory (such as RAM), non-volatile memory (such as ROM, flash memory, etc.) or any combination thereof. System memory 506 may include an operating system 520, one or more applications 522, and program data 524. Application 522 may include instructions 526 to carry out drug data analytic and patient risk scoring processes that are arranged to perform functions as described herein including those described with respect to process 200 of FIG. 2. Program data 524 may include drug-related casualty and patient data that may be useful for developing an abandoned patient model as is described herein. In some embodiments, application 522 may be arranged to operate with program data 524 on operating system 520 such that implementations of risk stratification in, e.g., healthcare systems, may be provided as described herein. This described basic configuration 502 is illustrated in FIG. 5 by those components within the inner dashed line.

Computing device 500 may have additional features or functionality, and additional interfaces to facilitate communications between basic configuration 502 and any required devices and interfaces. For example, a bus/interface controller 530 may be used to facilitate communications between basic configuration 502 and one or more data storage devices 532 via a storage interface bus 534. Data storage devices 532 may be removable storage devices 536, non-removable storage devices 538, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 506, removable storage devices 536 and non-removable storage devices 538 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of computing device 500.

Computing device 500 may also include an interface bus 540 for facilitating communication from various interface devices (e.g., output devices 542, peripheral interfaces 544, and communication devices 546) to basic configuration 502 via bus/interface controller 530. Example output devices 542 include a graphics processing unit 548 and an audio processing unit 550, which may be configured to communicate to various external devices such as a display or speakers via one or more A/V ports 552. Example peripheral interfaces 544 include a serial interface controller 554 or a parallel interface controller 556, which may be configured to communicate with external devices such as input devices (e.g., keyboard, mouse, pen, voice input device, touch input device, etc.) or other peripheral devices (e.g., printer, scanner, etc.) via one or more I/O ports 558. An example communication device 546 includes a network controller 560, which may be arranged to facilitate communications with one or more other computing devices 562 over a network communication link via one or more communication ports 564.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 500 may be implemented as a portion of a small-form factor portable (or mobile) electronic device such as a cell phone, a tablet, a personal data assistant (PDA), a personal media player device, a wireless web-watch device, a personal headset device, an application specific device, or a hybrid device that include any of the above functions. Computing device 500 may also be implemented as a personal computer including both laptop computer and non-laptop computer configurations.

The foregoing description is presented to enable one of ordinary skill in the art to make and use the disclosed embodiments and modifications thereof, and is provided in the context of a patent application and its requirements. Various modifications to the disclosed embodiments and the principles and features described herein will be readily apparent to those of ordinary skill in the art. Thus, the present disclosure is not intended to limit the invention to the embodiments shown; rather, the invention is to be accorded the widest scope consistent with the principles and features described herein.

We claim:

1. A method to stratify risks for adverse health outcomes, comprising:
aggregating data sets from a predetermined period of time from health, social, and environmental resources to collect statistical reports for maternal and infant health, behavior, and/or demographic data;
analyzing the aggregated data sets with a geospatial data analytic platform to establish a stratification for identifying mothers and infants at high risk of facing maternal mortality, maternal morbidity, infant mortality, or low birth weight for a child, wherein the analyzing comprises:
adjusting at least two variables within the aggregated data sets;
standardizing the at least two variables in the aggregated data sets to control differing data gathering capacities from the data sets; and
executing an iterative correlation and a regression analysis to determine geospatial contributors of the maternal mortality, the maternal morbidity, the infant mortality, and the low birth weight for the child to identify the high risk mothers and infants based on the at least two variables, wherein a positive degree of correlation between the at least two variables is used to quantify individual risk factors of the mothers and the infants for the maternal mortality, the maternal morbidity, the infant mortality, and the low birth weight for the child;
geospatially mapping the geospatial contributors of the maternal mortality, the maternal morbidity, the infant mortality, and the low birth weight for the child by visually representing the at least two variables on a map, wherein the mapping includes mapping the at least two variables having the positive degree of correlation as relevant numerators and denominators against each other to facilitate identification of key localities of at-risk mothers; and
altering social and health interventions and policies directed to the at-risk mothers to reduce the maternal mortality, the maternal morbidity, the infant mortality, and the low birth weight for a child, including identifying the specific in-community locations where the delivery of clinical care will have the greatest impact on reducing preventable maternal and child health complications.

2. The method of claim 1, wherein the data sets include panel data that are observable over time.

3. The method of claim 1, wherein the aggregating includes sorting the data sets based on variables including municipality, marital status at time of birth, infant mortality, and preterm birth.

4. The method of claim 1, wherein the at least two adjusted variables within the aggregated data sets include age and gender.

5. The method of claim 4, wherein the adjusting is based on population distribution across subject municipalities.

6. The method of claim 1, wherein the adjusting results in extraction of data for female subjects of child-bearing age.

7. The method of claim 1, wherein the method is implemented as computer-readable instructions stored upon a non-transitory computer-readable medium, executable by one or more processors.

8. A non-transitory computer-readable medium having executable instructions stored thereon that, upon execution, cause one or more processors to:
   aggregate health data regarding a general population in a particular municipality over a predetermined period of time from health, social, and environmental resources to collect statistical reports for maternal and infant health, behavior, and/or demographic data;
   analyze the aggregated data sets using a geospatial data analytic platform to establish a stratification for identifying mothers and infants at high risk of facing maternal mortality, maternal morbidity, infant mortality, or low birth weight for a child, which comprises:
   adjusting at least two variables within the aggregated health data to eliminate subjects outside of an area of interest;
   standardizing the at least two variables in the aggregated data sets to control differing data gathering capacities from the data sets; and
   executing an iterative correlation and regression analysis to determine geospatial contributors of the maternal mortality, the maternal morbidity, the infant mortality, and the low birth weight for the child to identify high-risk mothers and infants based on the at least two variables, wherein a positive degree of correlation between the at least two variables is used to quantify individual risk factors of the mothers and the infants for the maternal mortality, the maternal morbidity, the infant mortality, and the low birth weight for the child;
   geospatially map the geospatial contributors of the maternal mortality, the maternal morbidity, the infant mortality, and the low birth weight for the child by visually representing the at least two variables on a map, wherein the mapping includes mapping the at least two variables having the positive degree of correlation as relevant numerators and denominators against each other to facilitate identification of key localities of at-risk mothers; and
   alter health policies directed to the at-risk mothers to reduce the maternal mortality, the maternal morbidity, the infant mortality, and the low birth weight for a child, including identifying the specific in-community locations where the delivery of clinical care will have the greatest impact on reducing preventable maternal and child health complications.

9. The computer-readable medium of claim 8, wherein the health, social, and environmental data is aggregated based on variables including marital status at time of birth, infant mortality, and preterm birth.

10. The computer-readable medium of claim 8, wherein the at least two adjusted variables within the aggregated data sets include age and gender.

11. The computer-readable medium of claim 8, wherein the adjusting is based on population distribution across the particular municipality.

12. The computer-readable medium of claim 8, wherein the eliminated subjects are not female and are at least beyond child-bearing age.

13. The computer-readable medium of claim 8, wherein the iterative correlation and regression analysis includes quantifying a degree of correlation between individual risk factors against at least one relevant adverse outcome during pregnancy with a Pearson product-moment correlation coefficient.

14. The computer-readable medium of claim 8, wherein the processors are incorporated within a healthcare records system as well as other systems that track and monitor the health status of expecting mothers.

* * * * *